United States Patent [19]
Claes et al.

[11] Patent Number: 5,566,828
[45] Date of Patent: Oct. 22, 1996

[54] LOCKING PACKAGE FOR A SYRINGE

[75] Inventors: Paul Claes, Beveren; Leo De Bondt, Breendonk; Walter Van Giel, Aartselaar, all of Belgium

[73] Assignee: The Upjohn Company, Kalamazoo, Mich.

[21] Appl. No.: 390,964

[22] Filed: Feb. 21, 1995

[51] Int. Cl.$^6$ ............ B65D 85/20; B65D 55/00
[52] U.S. Cl. ............ 206/570; 70/63; 206/1.5; 206/365
[58] Field of Search ............ 70/63; 206/1.5, 206/365–367, 370, 438, 570

[56] References Cited

U.S. PATENT DOCUMENTS

| | | | |
|---|---|---|---|
| 3,149,717 | 9/1964 | Castlli | 206/365 |
| 3,439,796 | 4/1969 | Zykoski | 206/366 |
| 3,489,268 | 1/1970 | Meierhoefer | 206/366 |
| 3,499,458 | 2/1970 | Meierhoefer | 206/366 |
| 3,727,749 | 4/1973 | Martin | 206/366 |
| 4,425,999 | 1/1984 | MacDonald | 206/444 |
| 4,658,955 | 4/1987 | Eichner | 206/307 |
| 4,921,096 | 5/1990 | McFarlane | 206/349 |
| 4,969,554 | 11/1990 | Sawaya | 206/370 |
| 4,979,616 | 12/1990 | Clanton | 206/364 |
| 5,024,323 | 6/1991 | Bolton | 206/63.3 |
| 5,024,326 | 6/1991 | Sandel et al. | 206/366 |
| 5,133,454 | 7/1992 | Hammer | 206/364 |
| 5,156,267 | 10/1992 | Yates, Jr. et al. | 206/364 |
| 5,293,993 | 3/1994 | Yates, Jr. et al. | 206/365 |

FOREIGN PATENT DOCUMENTS

| | | | |
|---|---|---|---|
| 0367422 | 12/1994 | European Pat. Off. . | |
| 416673 | 12/1946 | Italy | 206/435 |

Primary Examiner—Jimmy G. Foster
Attorney, Agent, or Firm—Flynn, Thiel, Boutell & Tanis, P.C.

[57] ABSTRACT

A locking package structure wherein the package will provide a convenient and safe disposable receptacle for the syringe and the needle thereon and which can then be closed so as to prevent the syringe and needle from being a hazard. The open box receives the used syringe at the bedside and then can be snapped shut and locked for a safe disposal. The wall thickness of the package is thick enough so that the needle on the syringe cannot readily puncture the wall of the package and thus provides a safe disposal unit for the needle. A locking key is provided for locking the package so that access to the used syringe within the package cannot be attained after the locking key has been inserted into and lockingly engages the covers.

8 Claims, 4 Drawing Sheets

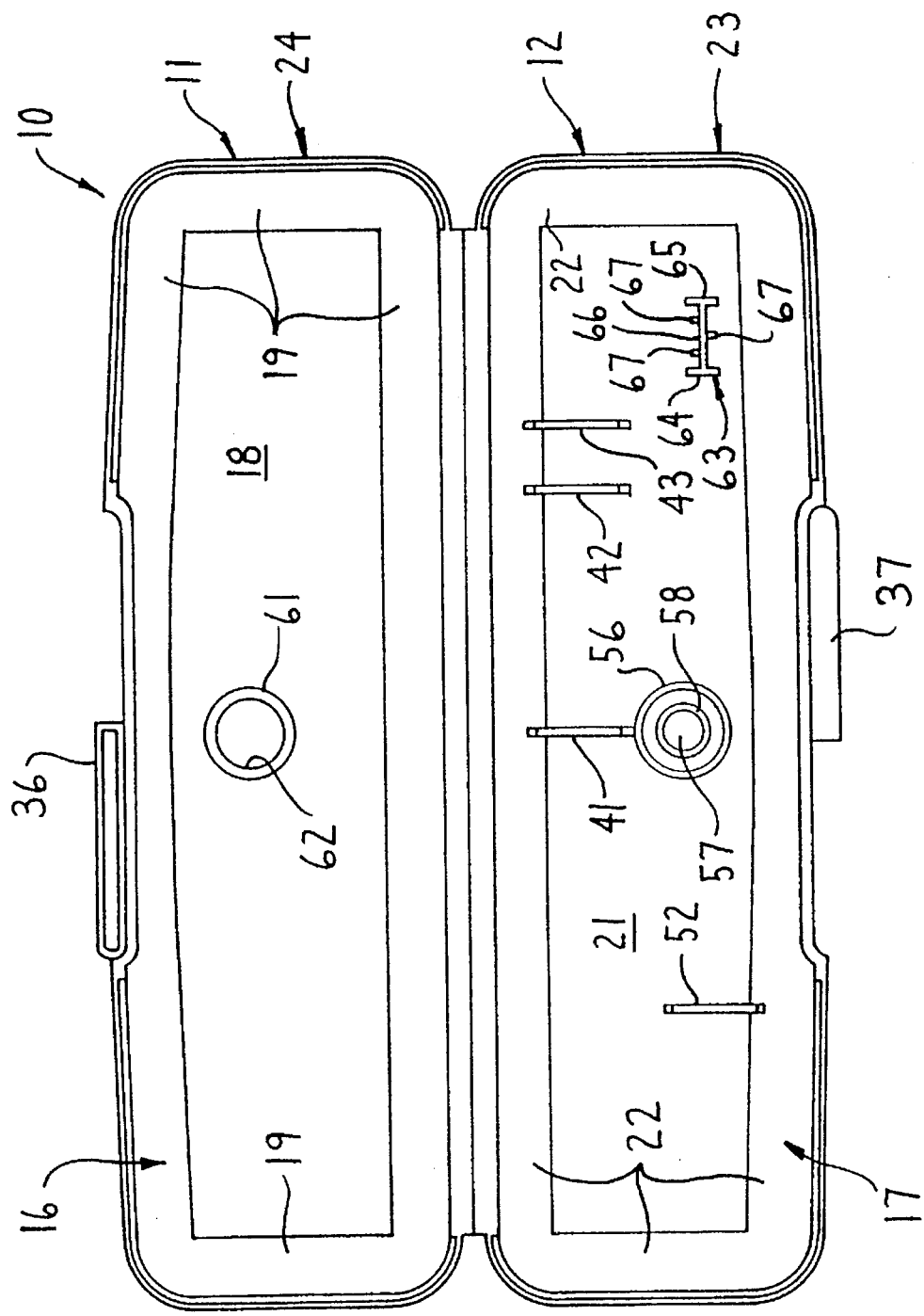

LOCKING PACKAGE FOR A SYRINGE

FIELD OF THE INVENTION

This invention relates to a locking container and, more particularly, to a locking container adapted for use in holding a syringe, a vial and a locking key, the locking key being used to lock the locking container in the closed condition after the placement therein of a used syringe.

BACKGROUND OF THE INVENTION

It has longs been realized in the health care industry that the handling of syringes can be problematic due to the accidental pricking and sticking of fingers, arms and other parts of the body by contaminated needles after syringes are used to administer drugs or to draw blood from patients. This problem has become particularly acute with the recent concern about Acquired Immunodeficiency Syndrome, or "AIDS" as well as periodic outbreaks of various strains of hepatitis. Patents that are known and which discuss these types of problems are U.S. Pat. Nos. 4,969,554, 4,979,616, 5,024,323, 5,024,326, 5,133,454, 5,156,267, 5,293,993 and EP-367 422.

Accordingly, it is an object of the invention to provide a locking package or container having a pair of cover members hingedly interrelated and movable between open and closed positions to permit access to a syringe receiving cavity located between the cover members, which cover members have structure thereon adapted to receive a locking key therein to lock the two cover members together in the closed position thereby denying convenient access to the contents of the now locked container.

It is a further object of the invention to provide a locking container, as aforesaid, which has syringe holding structure therein as well as a locking key holding structure with an elongated locking key removably stored on the locking key holding structure which, when the cover members have been moved to the open position, allow access to a syringe held by the syringe holding structure and access to the locking key held by the locking key holding structure.

It is a further object of the invention to provide a locking container, as aforesaid, wherein one of the cover members has a vial supporting structure thereon which can be accessed when the cover members have been moved to the open position.

SUMMARY OF THE INVENTION

The objects and purposes of the invention are met by providing a locking package structure wherein the package will provide a convenient and safe disposable receptacle for the syringe and the needle thereon and which can then be closed so as to prevent the syringe and needle from being a hazard. The open box receives the used syringe at the bedside and then can be snapped shut and locked for a safe disposal. The wall thickness of the package is thick enough so that the needle on the syringe cannot readily puncture the wall of the package and thus provides a safe disposal unit for the needle. A locking key is provided for locking the package so that access to the syringe within the package cannot be attained as long as the locking key has been inserted into and lockingly engages the covers.

BRIEF DESCRIPTION OF THE DRAWINGS

Other objects and purposes of this invention will be apparent to persons acquainted with apparatus of this general type upon reading the following specification and inspecting the accompanying drawings, in which:

FIG. 6 is a top view of the locking container in the open position illustrated in FIG. 1.

DETAILED DESCRIPTION

Figure 1:
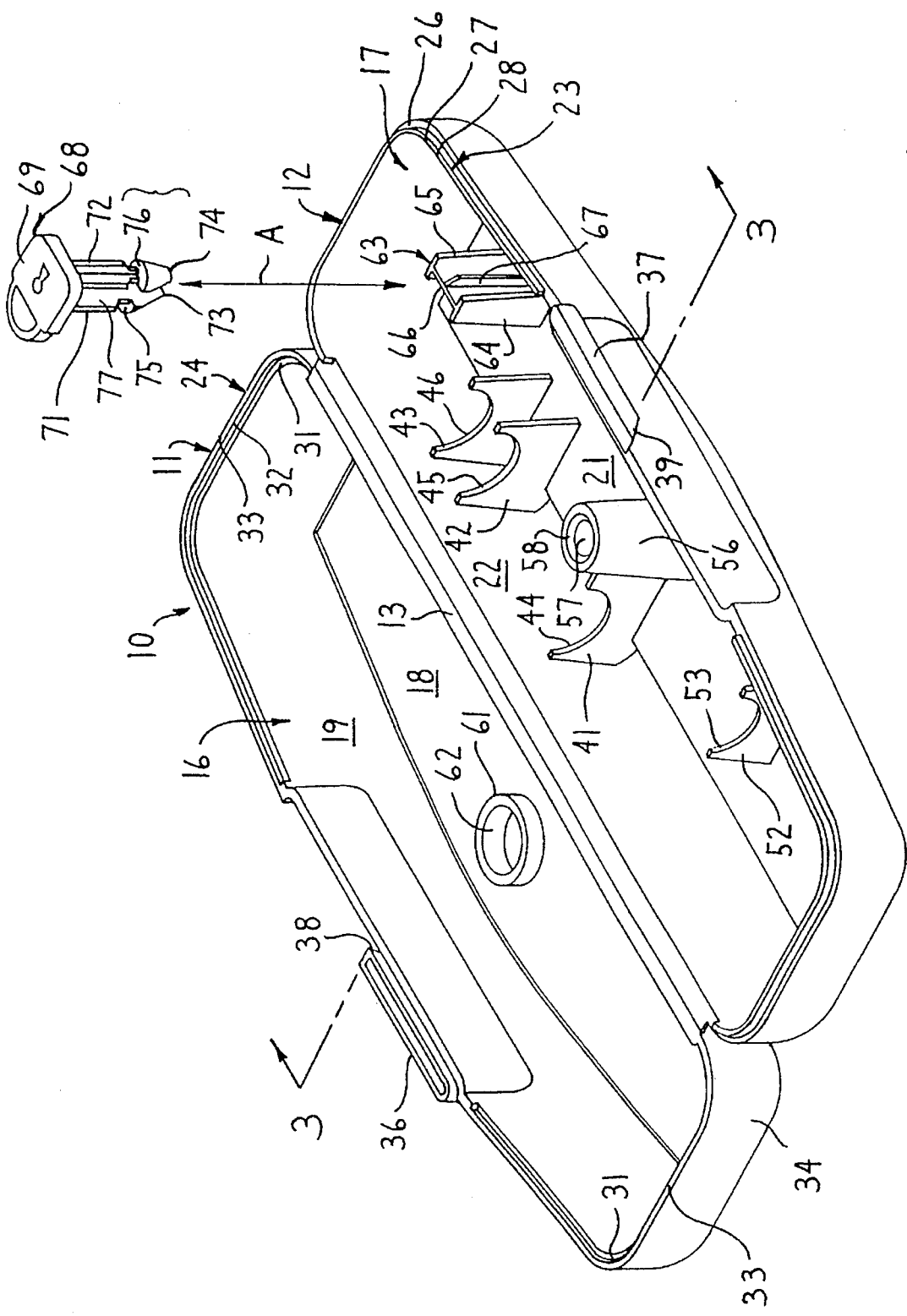
FIG. 1 is an isometric view of a locking package or container in the open position, which locking container embodies the invention.

Certain terminology Will be used in the following description for convenience in reference only and will not be limiting The words "up", "down", "right" and "left" will designate directions in the drawings to which reference is made. The words "in" and "out" will refer to directions toward and away from, respectively, the geometric center of the apparatus and designated parts thereof. Such terminology will include derivatives and words of similar import.

A locking container 10 is illustrated in the drawings and embodies the invention. More particularly, the locking container 10 includes a pair of cover members 11 and 12 connected to each other through an integral segment 13 defining a living hinge. Each cover member 11 and 12 has a cavity 16 and 17, respectively, therein. The cavity 16 includes a bottom wall 18 surrounded by an upstanding sidewall 19. The corners of the upstanding sidewall 19 are rounded and the over all shape of the cavity 16 is somewhat rectangular. The cavity 17 in the cover member 12 is generally identical to the cavity 16. More specifically, the cavity 17 has a bottom wall 21 and an upstanding sidewall 22 surrounding the bottom wall 21. The corners of the sidewall 22 are also rounded and the upper edge 23 conforms to the upper edge 24 of the sidewall 19. In this particular embodiment, the edge 23 has an outwardly facing step defining a generally horizontal surface 26 and a contiguous vertically upstanding surface 27 terminating in an upper rim 28 adjacent the internal surface of the upstanding sidewall 22. The edge 24 on the cover member 11 has an internally facing step defined by a horizontally extending surface 31 and a contiguous upstanding vertical surface 32 terminating in a rim 33 adjacent the exterior surface 34 of the cover member 11. When the cover members 11 and 12 are pivoted about the living hinge 13 to the closed position illustrated in FIG. 5, the rim 33.will seat on the horizontal surface 26 and the vertical surfaces 27 and 32 will oppose one another. In addition, the rim 28 will seat on the horizontal surface 31 to define a labyrinth type seal.

The cover member 11 includes a clasp 36 and the cover member 12 includes a conforming clasp 37 which, when the cover members 11 and 12 are in the closed position, operatively engage one another at their respective inclined surfaces 38 and 39 so as to temporarily hold the cover members 11 and 12 in the closed position.

The cavity 17 in the cover member 12 includes a plurality of upstanding, thin wall, supports 41, 42 and 43 at the juncture between the bottom wall 21 and the segment of the upstanding wall 22 adjacent the living hinge 13. Each support 41, 42 and 43 includes an arcuate depression 44, 45 and 46 in the upper edge thereof, the radius of such arc being such as to conform with the exterior of a syringe barrel 47 of a syringe assembly 48 illustrated in FIG. 2. The syringe assembly 48 includes the aforesaid barrel 47, a plunger 49 movable into the interior of the barrel 47 and a needle encased in a shroud 51 at the end of the barrel 47 remote from the plunger. The syringe assembly 48 is of a conventional construction and no further discussion concerning it will be presented herein.

Figure 2:
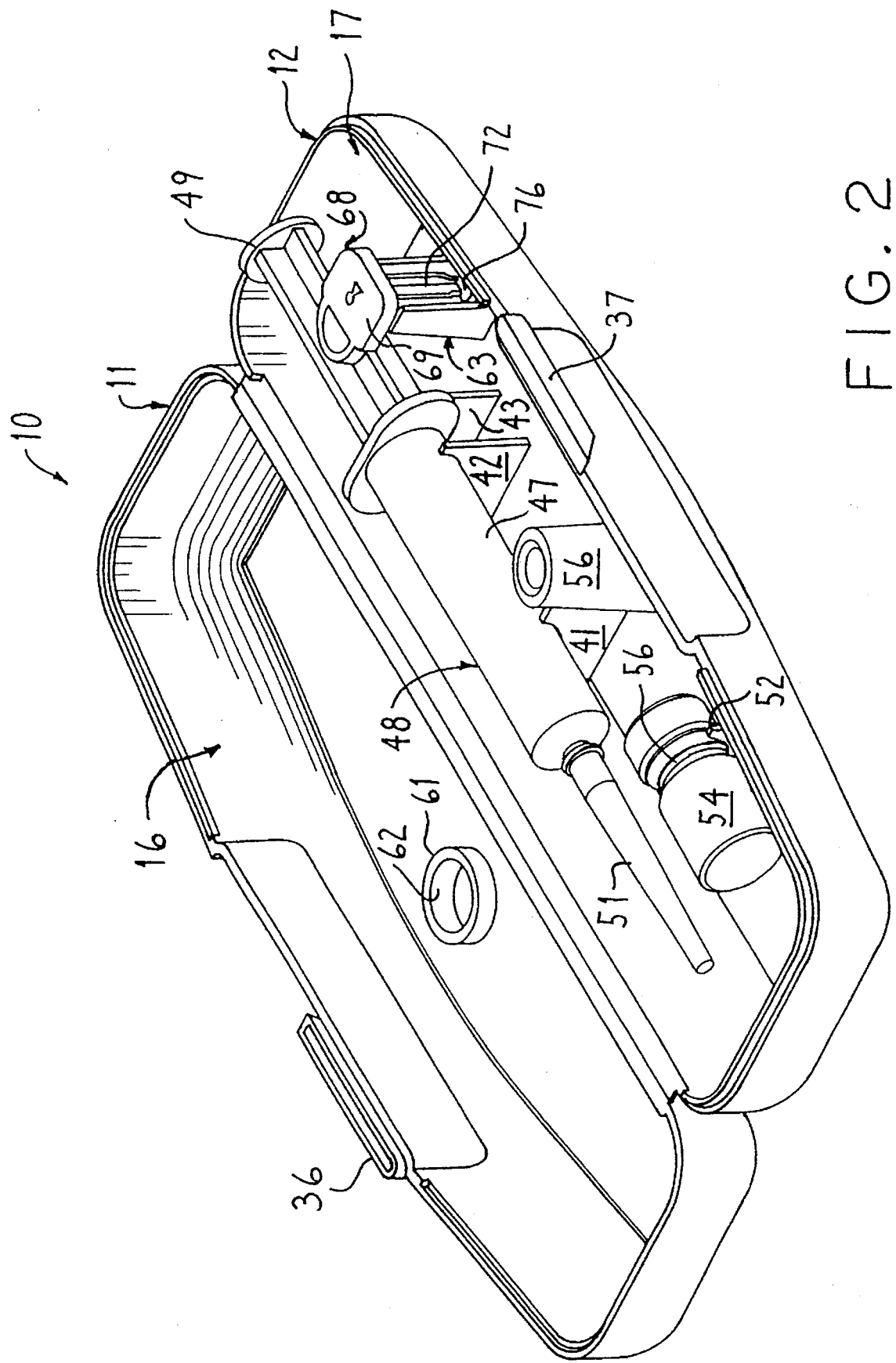
FIG. 2 is an isometric view of the locking container illustrated in FIG. 1 but having a syringe, vial and locking key shown in a cavity of one of the cover members.
Figure 3:
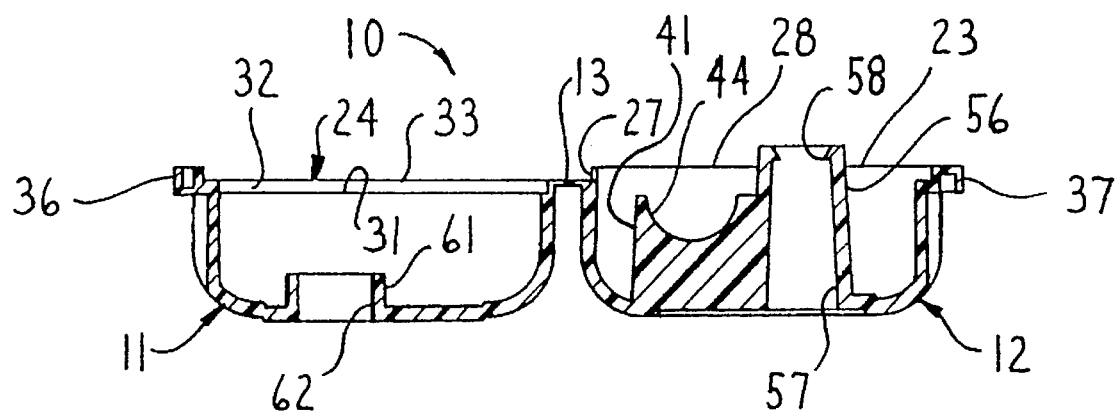
FIG. 3 is a sectional view taken along the line 3—3 of FIG. 1.
Figure 5:
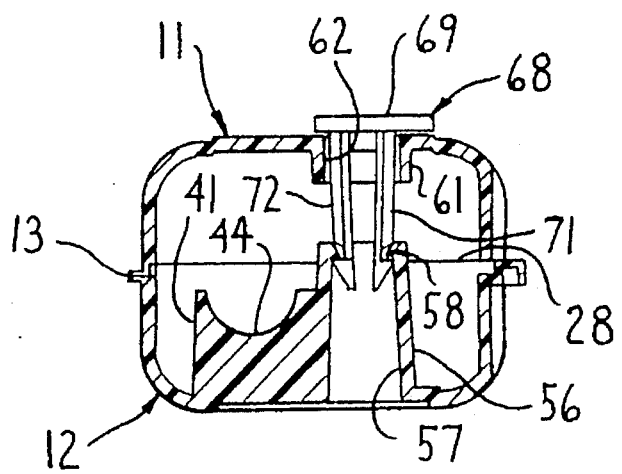
FIG. 5 is a sectional view of the locking container illustrated in FIG. 3 but with the cover members illustrated in the closed position and the locking key in place to lock the cover members together.

A further thin wall support 52 is upstanding from the bottom wall 21 at the juncture between the bottom wall 21 and the portion of the sidewall 22 containing the clasp 37. The support 52, like the supports 41, 42 and 43 has an arcuate depression 53 in the upper edge thereof. As illustrated in FIG. 2, the cavity 17 is adopted to hold a vialvin a reduced diameter neck 56thereof being received in the arcuate depression 53. As is illustrated in FIGS. 3 and 5, each of the upstanding supports 41, 42, 43 and 52 are spaced inwardly from the upstanding sidewall 22.

The cavity 17 further includes an upstanding hollow sleeve 56 having a through opening 57 extending centrally therethrough. In this particular embodiment, the hollow sleeve 56 is somewhat frustoconical in shape, the larger diameter end being contiguous with the bottom wall 21 of the cover member 12 and the smaller diameter end terminating at an elevation slightly higher than the rim 28 as illustrated in FIGS. 3 and 5. The through opening 57 has, adjacent the end thereof remote from the bottom wall 21 a radially inwardly extending bead 58 defining a latch.

The bottom wall 18 of the cover member 11 has an upstanding hollow sleeve 61 provided thereon, which hollow sleeve has a through opening 62 extending centrally therethrough. The upper end of the hollow sleeve 61 terminates well below the rim 33 when the cover members 11and 12 are in the closed position as illustrated in FIGS. 3 and 5, the through opening 62 becoming coaxially oriented with respect to the through opening 57. A separation exists between the distal ends of the hollow sleeves 56 and 61 as illustrated in Figure 5.

The bottom wall 21 of the cavity 17 includes an upstanding support 63. The upstanding support 63 includes a pair of parallel sidewalls 64 and 65 and an interconnecting wall 66 joined to the sidewalls 64 and 65 at about the mid-length thereof so as to define an H-shape. A plurality of ribs 67 project outwardly from opposite facing sides of the interconnecting wall 66 as illustrated in FIG. 6.

Figure 4:
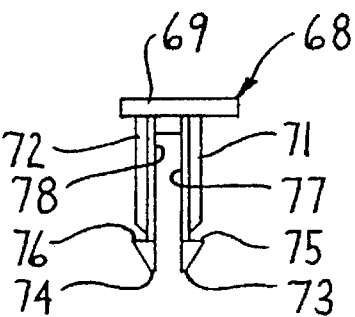
FIG. 4 is a side elevational view of a locking key embodying the invention.

A locking key (FIGS. 1 and 4) is provided and includes an enlarged head 69 and a pair of parallel depending legs 71 and 72 each terminating at a respective distal end 73 and 74 in respective shoulders 75 and 76 which each define a catch adapted to operatively engage the latch bead 58 at the distal end of the hollow sleeve 56. The legs 71 and 72 have opposing flat surfaces 77 and 78. The opposing flat surfaces 77 and 78 are adapted to slidingly engage the distal end of the ribs 67 provided on the interconnecting wall 66 extending between the sidewalls 64 and 65 of the support 63 in order to support the locking key on the support 63 as illustrated in FIG. 2. The locking key 68 is prevented from moving sideways by the sidewalls 64 and 65. The only way that the key 68 can be removed from the support 63 is by moving the key 68 relative to the support 63 along the direction of the arrow A.

In this particular embodiment, the enlarged head 69 of the locking key 68 is in the shape of a pad lock to symbolize to the user that the locking key 68 is to perform the locking task. More specifically, and referring to FIG. 5, when the cover members 11 and 12 are in the closed position and the through openings 57 and 62 are axially aligned, the locking key 68 is oriented so that the legs 71 and 72 extend first through the through opening 62 and thence past the latch bead 58 in the through opening 57 until the shoulders 75 and 76 become oriented beneath the latch bead 58. The locking key 68 and particularly the legs 71 and 72 thereof are elastically yieldable to facilitate a movement of the shoulders 75 and 76 past the locking bead 58 and become securely positioned beneath the locking bead at the time that the enlarged head 69 comes into engagement with the exterior surface 34 of the cover member 11. The locking container is now locked.

In normal use, and when it is time to gain access to the syringe assembly 48 and vial 54 inside the locking container 10, the engaged clasps 36 and 37 will be released so as to facilitate a movement of the cover member 11 relative to the cover member 12 to the open position illustrated in FIG. 2. The syringe assembly 48 and the vial 54 can be removed from the cavity 17. Following a usage of the syringe, it will be desired to dispose of the syringe in a safe manner. The used syringe assembly 48 is replaced into the cavity 17 on the supports 41, 42 and 43 and, if desired, the vial replaced on to the support 52. Thereafter, the locking key 68 can be moved upwardly away from the support 63 in direction of the arrow A and to a position illustrated in FIG. 1. Thereafter, the cover members 11 and 12 can be moved to the closed position illustrated in FIG. 5 so that the locking key 68 can be inserted into the now axially aligned through openings 57 and 62 to cause the shoulders 75 and 76 to become oriented beneath the latch bead 58 as described above.

The wall thickness of the cover members 11 and 12 is sufficiently thick so as to prevent an exposed needle from inadvertently becoming stuck through the sidewall of the material of the cover members.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A locking container for a syringe, comprising:

means defining a syringe receiving cavity including a pair of cover members each having an outer surface extremity, at least part of one of said pair of cover members being movable relative to the other cover member between an opened and a closed condition by means of an integral hinged assembly to permit access to said syringe receiving cavity located therebetween;

syringe holding means on one of said pair of cover members and oriented in said syringe receiving cavity;

locking key holding means on one of said pair of cover members and oriented in said syringe receiving cavity;

an elongated locking key removably stored on said locking key holding means and having thereon a catch at one end and an enlarged head at the other end;

means defining a pair of axially aligned holes when said cover members are in said closed position, one of said holes being provided through one of said pair of cover members and the other of said holes being provided through the other of said pair of cover members; and latch means fixedly oriented in one of said aligned two holes for operative engagement with said catch when said enlarged head contacts said outer surface extremity of the other of said pair of cover members in a region adjacent the other of said pair of holes to effect a locking of said cover members together in said closed position;

whereby a movement of said cover members to said opened position will provide access to the syringe and said locking key oriented in said syringe receiving cavity and facilitating a removal of the syringe and said locking key from said syringe receiving cavity, a movement of said cover members to said closed position causing the syringe, if soiled and placed back into said syringe receiving cavity, to become housed in said syringe receiving cavity, said pair of holes relatively movably receiving therein said end of said locking key having said catch until said catch operatively engages said latch means and said enlarged head contacts said outer surface extremity, at which time said locking key is rendered nonmovable in said holes and said cover members are hence forth locked together in said closed position.

2. The locking container according to claim 1, wherein said locking key holding means includes an upstanding post means; and wherein said elongated locking key includes post gripping means for operatively engaging said post means.

3. The locking container according to claim 2, wherein said post means has a pair of parallel sidewalls interconnected by an intermediate wall extending perpendicular therebetween; and wherein said post gripping means includes a pair of spaced apart and elastically yieldable legs appended to a common side of said enlarged head, said legs straddling said intermediate wall when said key is stored in said syringe receiving cavity.

4. The locking container according to claim 1, wherein said hole having said latch means fixedly oriented therein includes means defining an upstanding hollow sleeve integrally formed in said receiving cavity cavity and on one of said pair of cover members, said hollow sleeve having a first internal diameter, said latch means being defined by an internally projecting rim projecting into said hole to a second internal diameter dimension less than said first diameter and being oriented adjacent a distal end of said sleeve.

5. The locking container according to claim 1, wherein said pair of cover members each include a clasp member releasably engageable with the other to temporarily hold said cover members in said closed position.

6. The locking container according to claim 1, wherein one of said cover members includes a vial holder oriented in said cavity.

7. The locking container according to claim 6, wherein said syringe holding means, said locking key holder and said vial holder are provided on the same said cover member.

8. A locking container for a syringe, comprising:

means defining a syringe receiving cavity including a pair of cover members each having an outer surface extremity, at least part of one of said pair of cover members being movable relative to the other cover member between an opened and a closed condition by means of an integral hinged assembly to permit access to said syringe receiving cavity located therebetween;

syringe holding means on one of said pair of cover members and oriented in said syringe receiving cavity;

an elongated locking key having thereon a catch at one end and an enlarged head at the other end;

means defining a pair of axially aligned holes when said cover members are in said closed position, one of said holes being provided through one of said pair of cover members and the other of said holes being provided through the other of said pair of cover members; and latch means fixedly oriented in one of said aligned two holes for operative engagement with said catch when said enlarged head contacts said outer surface extremity of the other of said pair of cover members in a region adjacent said the other of said pair of holes to effect a locking of said cover members together in said closed position;

whereby a movement of said cover members to said opened position will provide access to the syringe oriented in said syringe receiving cavity and facilitating a removal of the syringe from said syringe receiving cavity, a movement of said cover members to said closed position causing the syringe, if soiled and placed back into said syringe receiving cavity, to become housed in said syringe receiving cavity, said pair of holes relatively movably receiving therein said end of said locking key having said catch until said catch operatively engages said latch means and said enlarged head contacts said outer surface extremity, at which time said locking key is rendered nonmovable in said holes and said cover members are hence forth locked together in said closed position.

* * * * *

UNITED STATES PATENT AND TRADEMARK OFFICE
CERTIFICATE OF CORRECTION

PATENT NO. : 5,566,828
DATED : October 22, 1996
INVENTOR(S) : Paul CLAES et al.

It is certified that error appears in the above-indentified patent and that said Letters Patent is hereby corrected as shown below:

Column 5, line 40; change "receiving cavity cavity" to ---syringe receiving cavity---.

Signed and Sealed this

Fifteenth Day of April, 1997

Attest:

BRUCE LEHMAN

Attesting Officer

Commissioner of Patents and Trademarks